United States Patent
Weichert et al.

[11] Patent Number: 5,965,744
[45] Date of Patent: Oct. 12, 1999

[54] ORTHO-SUBSTITUTED BENZOYLGUANIDINES, INCLUDING COMPOSITION AND METHODS OF USING THEM

[75] Inventors: Andreas Weichert, Egelsbach; Hans-Jochen Lang, Hofheim; Heinz-Werner Kleemann, Bad Homburg; Jan-Robert Schwark, Frankfurt; Wolfgang Scholz, Eschborn; Udo Albus, Florstadt, all of Germany

[73] Assignee: Hoeschst Aktiengesellschaft, Frankfurt am Main, Germany

[21] Appl. No.: 08/805,321

[22] Filed: Feb. 24, 1997

Related U.S. Application Data

[63] Continuation of application No. 08/657,434, Jun. 3, 1996, abandoned, which is a continuation of application No. 08/449,262, May 24, 1995, abandoned, which is a continuation of application No. 08/294,798, Aug. 25, 1994, abandoned.

[30] Foreign Application Priority Data

Aug. 27, 1993 [DE] Germany .............................. 43 28 869

[51] Int. Cl.$^6$ ...................... C07C 279/22; C07C 277/08; C07D 401/14; C07D 403/12; A61K 31/495; A61K 31/155
[52] U.S. Cl. ...................... 548/338.1; 514/280; 514/351; 514/399; 514/400; 514/617; 548/336.1; 564/37; 564/85; 564/153; 564/157; 564/183
[58] Field of Search .................................. 514/280, 351, 514/399, 400, 617; 564/153, 157, 85, 37, 183; 548/338.1, 336.1

[56] References Cited

U.S. PATENT DOCUMENTS

| | | | |
|---|---|---|---|
| 3,780,027 | 12/1973 | Cragoe et al. | 549/494 |
| 5,091,394 | 2/1992 | Englert et al. | 514/331 |
| 5,516,805 | 5/1996 | Lang et al. | 514/620 |

FOREIGN PATENT DOCUMENTS

| | | | |
|---|---|---|---|
| 0556673 | 8/1993 | European Pat. Off. | 564/183 |
| 0556674A1 | 8/1993 | European Pat. Off. | 564/183 |

OTHER PUBLICATIONS

Mildner et al., "Inhibition of Urease by Some Triazole, Urea, and Guanidine Derivatives," Croatica Chemica Acta, 46(1):79–82 (1974).

Englert et al II, Chemical Abstracts, vol. 115, #71158m (1991).

Lang et al II, Chemical Abstracts, vol. 119, #270818j (1993).

*Primary Examiner*—Floyd D. Higel
*Attorney, Agent, or Firm*—Finnegan, Henderson, Farabow, Garrett & Dunner, L.L.P.

[57] ABSTRACT

The present invention relates to ortho-substituted benzoylguanidines of the formula I, defined in the specification. The invention also embraces processes for making these compounds, as well as compositions and methods of using them. The compounds of the invention exhibit very good antiarrhythmic properties, making them useful in treating or preventing infarction, angina pectoris, and pathophysiological processes associated with ischemically induced damage.

12 Claims, No Drawings

ORTHO-SUBSTITUTED BENZOYLGUANIDINES, INCLUDING COMPOSITION AND METHODS OF USING THEM

This application is a continuation of Ser. No. 08/657,434, filed Jun. 3, 1996, now abandoned, which is a continuation of Ser. No. 08/449,262, filed May 24, 1995, now abandoned, which is a continuation of Ser. No. 08/294,798, filed Aug. 25, 1994, now abandoned.

The invention relates to benzoylguanidines of the formula I

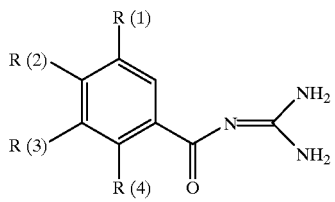

in which:
R(1) is H, F, Cl, Br, I, CN, $NO_2$, $(C_1-C_8)$-alkyl, $(C_3-C_8)$-cycloalkyl or $X_a$—$(CH_2)_b$—$(CF_2)_c CF_3$,
X is oxygen, S or NR(5),
a is zero or 1,
b is zero, 1 or 2,
c is zero, 1, 2 or 3,
  R(5) is H, $(C_1-C_4)$-alkyl or —$C_d H_{2d} R(6)$,
  d is zero, 1, 2, 3 or 4,
  R(6) is $(C_3-C_8)$-cycloalkyl, phenyl, bipheylyl or naphthyl, where the arrmatic radicals are not substituted or are substituted by 1 to 3 substituents selected from the group consisting of F, Cl, $CF_3$, methyl, methoxy or NR(7)R(8), with R(7) and R(8) being, independently, H or $(C_1-C_4)$-alkyl, or
R(1) is —SR(10), —OR(10) or —CR(10)R(11)R(12),
  R(10) is —$C_f H_{2f}$—$(C_3-C_8)$-cycloalkyl, —$(C_1-C_9)$-heteroaryl or phenyl, where the aromatic systems are unsubstituted or are substituted by 1 to 3 substituents selected from the group consisting of F, Cl, $CF_3$, $CH_3$, methoxy, hydroxyl, amino, methylamino or dimethylamino,
  f is zero, 1 or 2,
  R(11) and (R12), independently of each other, are defined as R(10) or are hydrogen or $(C_1-C_4)$-alkyl, or
R(1) is phenyl, naphthyl, biphenylyl or $(C_1-C_9)$-heteroaryl, the latter linked via C or N, and which are unsubstituted or are substituted by 1 to 3 substituents selected from the group consisting of F, Cl, $CF_3$, $CH_3$, methoxy, hydroxyl, amino, methylamino or dimethylamino, or
(R1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$,
  R(13) and R(14), identically or differently, are —$(CH_2)_g$—$(CHOH)_h$—$(CH_2)_i$—$(CHOH)_j$—R(17),
  R(17) is hydrogen, methyl or —$(CH_2)_g$—O—$(CH_2$—$CH_2 O)_h$—R(24), g, h and i, identically or differently, are zero, 1, 2, 3 or 4,
  j is 1, 2, 3 or 4,
  R(15) and R(16), identically or differently, are hydrogen, $(C_1-C_6)$-alkyl or, together with the carbon atom carrying them, a $(C_3-C_8)$-cycloalkyl,
  R(18) is phenyl, which is unsubstituted or is substituted by 1 to 3 substituents selected from the group consisting of F, Cl, $CF_3$, methyl, methoxy or NR(25) R(26) with R(25) and R(26) being H or $(C_1-C_4)$-alkyl, or
  R(18) is $(C_1-C_9)$-heteroaryl, which is unsubstituted or is substituted as phenyl, or
  R(18) is $(C_1-C_6)$-alkyl, which is unsubstituted or is substituted by 1 to 3 OH, or
  R(18) is $(C_3-C_8)$-cycloalkyl, and
  R(19), R(20), R(21), R(22) and R(23) are hydrogen or methyl,
  k is zero, 1, 2, 3 or 4,
  l is zero, 1, 2, 3 or 4,
  R(24) is H, $(C_1-C_6)$-alkyl, $(C_3-C_8)$-cycloalkyl or —$C_m H_{2m}$—R(18),
  m is 1, 2, 3 or 4,
R(2) and R(3) are defined as R(1), and
R(4) is $(C_1-C_3)$-alkyl, F, Cl, Br, I, CN or —$(CH_2)_n$—$(CF_2)_o$—$CF_3$,
n is zero or 1,
o is zero, 1 or 2,
as well as pharmaceutically tolerated salts thereof.

Compounds of the formula I are preferred in which:
R(1) is H, F, Cl, Br, CN, $NO_2$, $(C_1-C_8)$-alkyl, $(C_3-C_8)$-cycloalkyl or $X_a$—$(CF_2)_c$—$CF_3$,
X is oxygen or S,
a is zero or 1,
c is zero, 1, 2 or 3, or
R(1) is —SR(10) or —OR(10),
  R(10) is —$C_f H_{2f}$—$(C_3-C_8)$-cycloalkyl, —$(C_1-C_9)$-heteroaryl or phenyl, where the aromatic systems are unsubstituted or are substituted by 1 to 3 substituents selected from the group consisting of F, Cl, $CF_3$, $CH_3$, methoxy, hydroxyl, amino, methylamino or dimethylamino, f is zero or 1, or
R(1) is phenyl, naphthyl, biphenylyl or $(C_1-C_9)$-heteroaryl, the latter linked via C or N, and which are unsubstituted or are substituted by 1 to 3 substituents selected from the group consisting of F, Cl, $CF_3$, $CH_3$, methoxy, hydroxyl, amino, methylamino or dimethylamino, or
(R1) is —SR(13), —OR(13), —NHR(13), —NR(13)R(14), —C≡CR(18), —C[R(19)]=CR(18),
  R(13) and R(14), identically or differently, are —$(CH_2)_g$—$(CHOH)_h$—$(CH_2)_i$—$(CHOH)_j$—R(17),
  R(17) is hydrogen, methyl or —$(CH_2)_g$—O—$(CH_2$—$CH_2 O)_h$—R(24), g, h and i, identically or differently, are zero, 1 or 2,
  j is 1 or 2,
  R(18) is phenyl, which is unsubstituted or is substituted by 1 to 3 substituents selected from the group consisting of F, Cl, $CF_3$, methyl, methoxy or NR(25) R(26) with R(25) and
  R(26) being H or $(C_1-C_4)$-alkyl, or
  R(18) is $(C_1-C_9)$-heteroaryl, which is unsubstituted or is substituted as phenyl, or
  R(18) is $(C_1-C_6)$-alkyl, which is unsubstituted or is substituted by 1 to 3 OH, or
  R(18) is $(C_3-C_8)$-cycloalkyl, and
  R(19) is hydrogen or methyl,
R(2) and R(3) are defined as R(1), and
R(4) is $(C_1-C_2)$-alkyl, F, Cl, Br, CN or —$(CH_2)_n$—$(CF_2)_o$—$CF_3$,
n is zero or 1,
o is zero or 1, as well as pharmaceutically tolerated salts thereof.

Compounds of the formula I are particularly preferred in which:

R(1) is H, F, Cl, ($C_1$–$C_4$)-alkyl, ($C_5$–$C_6$)-cycloalkyl or $X_a$—$(CF_2)_c$—$CF_3$,
X is oxygen,
a is zero or 1,
c is zero or 1, or
R(1) is —SR(10) or —OR(10),
R(10) is ($C_4$–$C_6$)-cycloalkyl, quinolyl, isoquinolyl, pyridyl or phenyl, which is unsubstituted or is substituted by 1 to 3 substituents selected from the group consisting of F, Cl, $CF_3$, $CH_3$, methoxy, hydroxyl, amino, methylamino or dimethylamino, or
R(1) is phenyl, quinolyl, isoquinolyl, pyridyl or imidazolyl, bonded via C or N, which are unsubstituted or are substituted by 1 to 3 substituents selected from the group consisting of F, Cl, $CF_3$, $CH_3$, methoxy, hydroxyl, amino, methylamino or dimethylamino, or
(R1) is —C≡—CR(18),
R(18) is phenyl or ($C_5$–$C_6$)-cycloalkyl,
R(2) and R(3) are defined as R(1), and
R(4) is methyl, F, Cl or $CF_3$,
as well as pharmaceutically tolerated salts thereof.

($C_1$–$C_9$)-Heteroaryl is understood to mean radicals which are derived from phenyl or naphthyl, in which one or more CH groups are replaced by N and/or in which at least two neighboring CH groups (with the formation of a five-membered aromatic ring) are replaced by S, NH or O. In addition, one or both the atoms of the fusion site of bicyclic radicals (as in indolizinyl) can also be N atoms.

It applies, in particular, that ($C_1$–$C_9$)-heteroaryl is furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl.

If one of the substituents R(1) to R(4) contains one or more centers of asymmetry, these centers can have either the S-configuration or the R-configuration. The compounds can be present as optical isomers, as diastereomers, as racemates or as mixtures thereof.

Alkyl radicals can be either straight-chain or branched.

In addition, the invention relates to a process for preparing the compound I, which comprises reacting a compound of the formula II

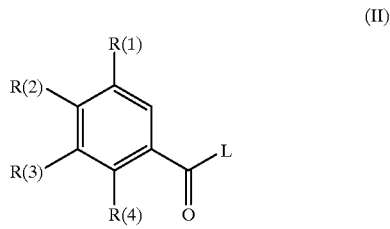

(II)

in which R(1) to R(4) have the given meaning and L is a leaving group which can readily be substituted nucleophilically, with guanidine.

The activated acid derivatives of the formula II, in which L is an alkoxy, preferably a methoxy, group, a phenoxy group, phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which, for their part, can in turn be prepared, in a manner known per se, from the underlying carboxylic acids (formula II, L=OR), for example using thionyl chloride.

In addition to the carbonyl chlorides of the formula II (L=Cl), further activated acid derivatives of the formula II can also be prepared, in a manner known per se, directly from the underlying benzoic acid derivatives (formula II, L=OH), such as, for example, the methyl esters of the formula II with L=$OCH_3$ by treating with gaseous HCl in methanol, the imidazolides of the formula II by treating with carbonyldiimidazole [L=1-imidazolyl, Staab, Angew. Chem. Int. Ed. Engl. 1, 351 to 367 (1962)], the mixed anhydrides II with Cl—$COOC_2H_5$ or tosyl chloride in the presence of triethylamine in an inert solvent, as well as the activation of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A series of suitable methods for preparing activated carboxylic acid derivatives of the formula II are given, with citation of the source literature, in J. March, Advanced Organic Chemistry, Third Edition (John Wiley & Sons, 1985), p. 350.

The reaction of an activated carboxylic acid derivative of the formula II with guanidine is effected, in a manner known per se, in a protic or aprotic organic solvent which is polar but inert. In this context, methanol, isopropanol or THF have proved to be suitable, at temperatures of from 20° C. up to the boiling temperature of these solvents, for use in the reaction of the methyl benzoates (II, L=OMe) with guanidine. Aprotic, inert solvents, such as THF, dimethoxyethane and dioxane, were advantageously employed in most of the reactions of compounds II with salt-free guanidine. However, water can also be used, while employing a base, such as, for example, NaOH, as solvent in the reaction of II with guanidine.

When L=Cl, an acid scavenger, for example in the form of excess guanidine, is advantageously added in order to bind the hydrohalic acid.

Some of the underlying benzoic acid derivatives of the formula II are known and are described in the literature. The unknown compounds of the formula II may be prepared by methods known from the literature. The resulting benzoic acids are reacted to give compounds I according to the invention in accordance with one of the above-described process variants.

The introduction of some substituents in the 3, 4, 5 and 6 positions is achieved by methods known from the literature involving palladium-mediated cross-coupling of aryl halides or aryl triflates with, for example, organo-stannanes, organoboronic acids or organoboranes or organocopper or organozinc compounds.

Benzoylguanidines I are in general weak bases and are able to bind acid with the formation of salts. Salts of all pharmacologically tolerated acids, for example halides, in particular hydrochlorides, lactates, sulfates, citrates, tartrates, acetates, phosphates, methanesulfonates and p-toluenesulfonates, are suitable acid addition salts.

The compounds I are substituted acylguanidines. The most prominent representative of the acylguanidines is the pyrazine derivative amiloride, which is used in therapy as a potassium-sparing diuretic agent. Numerous further compounds of the amiloride type are described in the literature, such as, for example, dimethylamiloride or ethylisopropylamiloride.

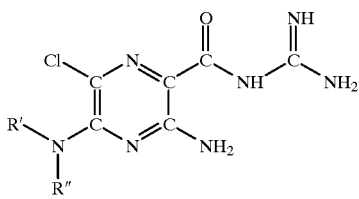

Amiloride: R', R"=H
Dimethylamiloride: R', R"=CH$_3$
Ethylisopropylamiloride: R'=CH$_2$H$_5$, R"=CH(CH$_3$)$_2$ In addition to this, investigations have become known which point to amiloride having antiarrhythmic properties (Circulation 79, 1257 to 1263 (1989)). However, a factor counting against any widespread use of amiloride as an antiarrhythmic agent is that this effect is only weakly expressed and is accompanied by hypotensive and saluretic effects, which latter side effects are undesirable when treating cardiac arrhythmia.

Indications that amiloride has antiarrhythmic properties were also obtained in experiments on isolated animal hearts (Eur. Heart J. 9 (suppl.1): 167 (1988) (book of abstracts)). Thus it was found, using rat hearts, for example, that amiloride was able to completely suppress artificially induced ventricular fibrillation. The above-mentioned amiloride derivative ethylisopropylamiloride was even more potent than amiloride in this model system.

Benzoylguanidines, which, however, do not carry any substituents located in the ortho position on the aromatic nucleus, are described in U.S. Pat. No. 5,091,394 (HOE 89/F 288) and in the German Patent Application P 42 04 575.4 (HOE 92/F 034).

In U.S. Pat. No. 3 780 027, acylguanidines are claimed which are structurally similar to the compounds of the formula I and which are derived from commercially available loop diuretics, such as bumetanide. Correspondingly, these compounds have been reported to have strong salidiuretic activity.

It was surprising, therefore, that the compounds according to the invention do not exhibit any undesirable and disadvantageous salidiuretic properties, but exhibit very good activity against arrhythmias of the type that occur, for example, in association with symptoms of oxygen deficiency. As a consequence of their pharmacological properties, the compounds are outstandingly suitable for use as antiarrhythmic pharmaceuticals having a cardioprotective component for the prophylaxis and treatment of infarction as well as for the treatment of angina pectoris, the compounds also inhibiting or strongly reducing, in a preventive manner, the pathophysiological processes in association with the occurrence of ischemically induced damage, in particular in association with the elicitation of ischemically induced cardiac arrhythmias. On account of their protective effects against pathological hypoxic and ischemic situations, the compounds of the formula I according to the invention can be used, as a consequence of inhibition of the cellular Na$^+$/H$^+$ exchange mechanism, as pharmaceuticals for treating all acute or chronic damage elicited by ischemia, or illnesses which are primarily or secondarily induced thereby. This applies to their use as pharmaceuticals for surgical interventions, e.g. in association with organ transplantations, it being possible to use the compounds to protect the organs in the donor before and during removal and to protect removed organs, for example when being treated with physiological bathing fluids or when being stored in these fluids, and also in association with transfer of the organs into the recipient subject. The compounds are likewise valuable protective pharmaceuticals for use when carrying out angioplastic surgical interventions, for example on the heart or on peripheral vessels. In accordance with their protective action against ischemically induced damage, the compounds are also suitable for use as pharmaceuticals for treating ischemias of the nervous system, in particular of the CNS, where they are suitable e.g. for the treatment of stroke or of cerebral edema. In addition to this, the compounds of the formula I according to the invention are likewise suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the vasculature. For this reason, the compounds of the formula I are suitable, as valuable therapeutic agents, for use in diseases in which cell proliferation represents a primary or secondary cause, and may therefore be used as antiatherosclerotic agents, and as agents against diabetic secondary complications, carcinomatous disorders, fibrotic disorders such as pulmonary fibrosis, hepatic fibrosis or renal fibrosis, and against organ hypertrophy and hyperplasia, in particular in hyperplasia or hypertrophy of the prostate.

The compounds according to the invention are efficacious inhibitors of the cellular sodium/proton antiporter (Na$^+$/H$^+$ exchanger), which, in numerous disorders (essential hypertension, atherosclerosis, diabetes, etc.), is also elevated in those cells which are readily accessible to measurement, such as, for example, in erythrocytes, blood platelets or leukocytes. The compounds according to the invention are therefore suitable for use as outstanding, simple, scientific tools, for example in their use as diagnostics for determining and differentiating particular forms of hypertension, but also for use in atherosclerosis, diabetes, proliferative disorders, and so on. In addition, the compounds of the formula I are suitable for use in preventive therapy for preventing the genesis of high blood pressure, for example of essential hypertension.

In this context, pharmaceuticals which contain a compound I can be administered orally, parenterally, intravenously or rectally, or by inhalation, the preferred route of administration being dependent on how the disorder manifests itself. In this context, the compounds I may be used alone or together with pharmaceutical auxiliary substances, both in the case of veterinary medicine and in the case of human medicine.

Owing to his specialist knowledge, the person skilled in the art is familiar with which auxiliary substances are suitable for the desired pharmaceutical formulation. In addition to solvents, gel-formers, suppository bases, tablet auxiliary substances, and other active-compound excipients, antioxidants, dispersing agents, emulsifiers, defoamers, taste corrigents, preservatives, solubilizers or dyes, for example, can be used.

In order to prepare a form for oral use, the active compounds are mixed with the additives which are suitable for the purpose, such as excipient substances, stabilizers or inert diluents, and converted by the customary methods into the forms suitable for administration, such as tablets, coated tablets, hard gelatin capsules or aqueous, alcoholic or oily solutions. Gum arabic, magnesia, magnesium carbonate, potassium phosphate, lactose, glucose or starch, in particular corn starch, for example, can be used as inert carriers. In this context, the preparation can be effected as dry or wet granules. Vegetable or animal oils, for example, such as sunflower oil or cod-liver oil, are suitable for use as oily carrier substances or as solvents.

For subcutaneous or intravenous administration, the active compounds, if desired together with the substances which are customary for the purpose, such as solubilizers, emulsifiers or additional auxiliary substances, are brought into solution, suspension or emulsion. Examples of suitable solvents are: water, physiological saline solution, or alcohols, for example ethanol, propanol or glycerol, and in addition sugar solutions as well, such as glucose or mannitol solutions, or else a mixture of the different said solvents.

Solutions, suspensions or emulsions of the active compound of the formula I in a pharmaceutically harmless solvent, such as, in particular, ethanol or water, or a mixture of such solvents, are suitable for use as a pharmaceutical formulation for administration in the form of aerosols or sprays, for example.

Depending on requirements, the formulation can also contain other further pharmaceutical auxiliary substances, such as surface active agents, emulsifiers and stabilizers, as well as a propellant. Such a preparation customarily contains the active compound in a concentration of about 0.1 to 10, in particular of about 0.3 to 3% by weight.

The dosage of the active compound of the formula I to be administered, and the frequency of the administration, depend on the strength and the duration of the effect of the compounds used; additionally also on the nature and severity of the disease to be treated, as well as on the sex, age, weight and individual responsiveness of the mammal to be treated.

On average, the daily dose of a compound of the formula I for a patient of about 75 kg in weight is at least 0.001 mg/kg, preferably 0.01 mg/kg, up to at most 10 mg/kg, preferably 1 mg/kg, of body weight. In acute episodes of the disorder, for example immediately after suffering a cardiac infarction, even higher, and in particular more frequent, dosages may also be necessary, for example up to 4 individual doses per day. In association with i.v. use, in particular, for example in the case of an infarction patient in intensive care, up to 200 mg per day may be necessary.

List of Abbreviations:
MeOH methanol
DMF N,N-dimethylformamide
RT room temperature
EA ethyl acetate (EtOAc)
m.p. melting point
THF tetrahydrofuran
eq. equivalent
CNS central nervous system Experimental Section
General Instructions for Preparing Benzoylguanidines (I)
Variant A: from Benzoic Acids (II, L=OH)

1.0 eq. of the benzoic acid derivative of the formula II is dissolved or suspended in anhydrous THF (5 ml/mmol) and 1.1 eq. of carbonyldiimidazole is then added. After stirring at RT for 2 hours, 5.0 eq. of guanidine are introduced into the reaction solution. After stirring overnight, the TEF is distilled off under reduced pressure (Rotavapor) and water is added to the mixture, which is then adjusted to pH 6 to 7 using 2N HCl, and the corresponding benzoylguanidine (formula I) is filtered off. The benzoylguanidines thus obtained can be converted into the corresponding salts by treatment with aqueous, methanolic or ethereal hydrochloric acid or other pharmacologically tolerated acids.

General Instructions for Preparing Benzoylguanidines (I)
Variant B: from Alkyl Benzoates (II, L=O-alkyl)

1.0 eq. of the alkyl benzoate of the formula II and 5.0 eq. of guanidine (free base) are dissolved in isopropanol or suspended in THF and heated at boiling point (typical reaction time 2 to 5 hours) until conversion is complete (thin-layer monitoring). The solvent is distilled off under reduced pressure (Rotavapor) and the residue is taken up in EA and washed 3× with $NaRCO_3$ solution. Drying takes place over $Na_2SO_4$, the solvent is distilled off in vacuo, and the residue is chromatographed on silica gel using a suitable eluent, e.g. EA/MeOH 5:1.

(Salt formation: cf. variant A)

EXAMPLE 1

2,3-Dichlorobenzoylguanidine hydrochloride: colorless crystals, m.p. 232° C. from 2,3-dichlorobenzoic acid in accordance with variant A

EXAMPLE 2

2-Fluoro-3-trifluoromethylbenzoylguanidine hydrochloride: colorless crystals, vitreous from 2-fluoro-3-trifluoromethylbenzoic acid in accordance with variant B

EXAMPLE 3

2,4-Dichlorobenzoylguanidine hydrochloride: colorless crystals, m.p. 242° C. from 2,4-dichlorobenzoic acid in accordance with variant A

EXAMPLE 4

2-Fluoro-4-trifluoromethylbenzoylguanidine hydrochloride: colorless crystals, m.p. 143 to 145° C. from 2-fluoro-4-trifluoromethylbenzoic acid in accordance with variant B

EXAMPLE 5

2,5-Dimethylbenzoylguanidine hydrochloride: colorless crystals, m.p. 247° C. from 2,5-dimethylbenzoic acid in accordance with variant A.

EXAMPLE 6

2,5-Dichlorobenzoylguanidine hydrochloride: colorless crystals, m.p. 209° C. from 2,5-dichlorobenzoic acid in accordance with variant A.

EXAMPLE 7

2,5-Bis(trifluoromethyl)benzoylguanidine hydrochloride: colorless crystals, m.p. 240 to 242° C. from 2,5-bis(trifluoromethyl)benzoic acid in accordance with variant A.

EXAMPLE 8

2-Fluoro-5-trifluoromethylbenzoylguanidine hydrochloride: colorless crystals, m.p. 168 to 170° C. from 2-fluoro-5-trifluoromethylbenzoic acid in accordance with variant A.

EXAMPLE 9

2-Chloro-5-trifluoromethylbenzoylguanidine hydrochloride: colorless crystals, m.p. 209–11° C. from 2-chloro-5-trifluoromethylbenzoic acid in accordance with variant A.

EXAMPLE 10

2-Fluoro-5-iodo-3-trifluoromethylbenzoylguanidine hydrochloride: colorless crystals, m.p. 197–200° C.

Synthesis Route:
a) 2-Fluoro-5-iodo-3-trifluoromethylbenzonitrile from 2-fluoro-3-trifluoromethylbenzonitrile by reaction with 1 equivalent of N-iodosuccinimide in 5 equivalents of trifluoromethanesulfonic acid at RT for 24 h, colorless crystals, m.p. 65–67° C.
b) 2-Fluoro-5-iodo-3-trifluoromethylbenzoic acid from a) by heating a mixture of conc. hydrochloric acid in glacial acetic acid, colorless crystals, m.p. 136–38° C.
c) 2-Fluoro-5-iodo-3-trifluoromethylbenzoylguanidine hydrochloride from b) in accordance with variant A

EXAMPLE 11

2,4-Difluorobenzoylguanidine hydrochloride: colorless crystals, m.p. 170–72° C. from 2,4-difluorobenzoic acid in accordance with variant A.

EXAMPLE 12

2,6-Difluorobenzoylguanidine hydrochloride: colorless crystals, m.p. 208–10° C. from 2,6-difluorobenzoic acid in accordance with variant A.

EXAMPLE 13

4-Fluoro-2-trifluoromethylbenzoylguanidine hydrochloride: colorless crystals, m.p. 155–57° C. from 4-fluoro-2-trifluoromethylbenzoic acid in accordance with variant A.

EXAMPLE 14

6-Fluoro-2-trifluoromethylbenzoylguanidine hydrochloride: colorless crystals, m.p. 178–80° C. from 6-fluoro-2-trifluoromethylbenzoic acid in accordance with variant A.

EXAMPLE 15

4-Imidazolyl-2-trifluoromethylbenzoylguanidine hydrochloride: colorless crystals, amorphous from 4-imidazolyl-2-trifluoromethylbenzoic acid in accordance with variant A.

EXAMPLE 16

2-Trifluoromethylbenzoylguanidine hydrochloride: colorless crystals, m.p. 225° C. from 2-trifluoromethylbenzoic acid in accordance with variant A.

EXAMPLE 17

2-Chlorobenzoylguanidine hydrochloride: colorless crystals, m.p. 161° C. from 2-chlorobenzoic acid in accordance with variant A.

EXAMPLE 18

2,3-Dichloro-4-methoxybenzoylguanidine hydrochloride: colorless crystals, m.p. 227° C. from 2,3-dichloro-4-methoxybenzoic acid in accordance with variant A.

EXAMPLE 19

2-Chloro-5-methylbenzoylguanidine hydrochloride: colorless crystals, m.p. 134° C. from 2-chloro-5-methylbenzoic acid in accordance with variant A.

Pharmacological Data:
Inhibition of the $Na^+/H^+$ Exchanger of Rabbit Erythrocytes
New Zealand White rabbits (Ivanovas) received a standard diet containing 2% cholesterol for six weeks in order to activate the $Na^+/H^+$ exchange and thus to be able to determine, by flame photometry, the $Na^+$ influx into the erythrocytes via $Na^+/H^+$ exchange. The blood was removed from the aural arteries and rendered incoagulable using 25 IU of potassium heparin. A part of each sample was used for the duplicate determination of the hematocrit by means of centrifugation. Aliquots of in each case 100 μl were used for measuring the initial $Na^+$ content of the erythrocytes.

In order to determine the amiloride-sensitive sodium influx, 100 μl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl) aminomethane). The erythrocytes were then washed three times with ice-cold $MgCl_2$/ouabain solution (mmol/ml: 112 $MgCl_2$, 0.1 ouabain) and hemolyzed in 2.0 ml of distilled water. The intracellular sodium content was determined by flame photometry.

The net influx of $Na^+$ was calculated from the difference between the initial sodium values and the sodium content of the erythrocytes following incubation. The amiloride-inhibitable sodium influx was calculated from the difference in the sodium content of the erythrocytes following incubation with and without amiloride $3 \times 10^{-4}$ mol/l. This method was also employed in the case of the compounds according to the invention.

Results
Inhibition of the $Na^+/H^+$ Exchanger:

| Example | $IC_{50}$ (mol/l) |
| --- | --- |
| 1 | greater than $10^{-6}$ |
| 2 | $2 \times 10^{-6}$ |
| 3 | $8 \times 10^{-6}$ |
| 4 | $3 \times 10^{-6}$ |
| 5 | $2 \times 10^{-6}$ |
| 6 | $1.5 \times 10^{-6}$ |
| 7 | $0.16 \times 10^{-6}$ |
| 8 | $0.7 \times 10^{-6}$ |
| 9 | $0.16 \times 10^{-6}$ |
| 10 | $0.09 \times 10^{-6}$ |

We claim:
1. A benzoylguanidine of the formula I

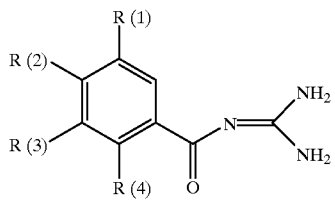

in which:
R(1) is H, F, Cl, Br, I, CN, $NO_2$, $(C_1-C_8)$-alkyl, $(C_3-C_8)$-cycloalkyl or $X_a-(CH_2)_b-(CF_2)_c-CF_3$,
X is oxygen, S or NR(5),
a is zero or 1,
b is zero, 1 or 2,
c is zero, 1, 2 or 3,
R(5) is H, $(C_1-C_4)$-alkyl or $-C_dH_{2d}R(6)$,
d is zero, 1, 2, 3 or 4,
R(6) is $(C_3-C_8)$-cycloalkyl, phenyl, biphenylyl or naphthyl, where the phenyl, biphenyl or naphthyl radicals are not substituted or are substituted by 1 to 3 substituents selected from the group consisting of F, Cl, $CF_3$, methyl, methoxy and NR(7)R (8), with R(7) and R(8) being, independently, H or (C$_1$–C$_4$)-alkyl, or R(1) is —SR(10), —OR(10) or —CR(10O)R(11)R(12), R(10) is —C$_f$H$_{2f}$—(C$_3$–C$_8$)-cycloalkyl, —(C$_1$–C$_9$)-heteroaryl or phenyl, where the heteroaryl or phenyl system is unsubstituted or is substituted by 1 to 3 substituents selected from the group consisting of F, Cl, CF$_3$, CH$_3$, methoxy, hydroxyl, amino, methylamino and dimethylamino, f is zero, 1 or 2, R(11) and (R12), independently of each other, are defined as R(10) or are hydrogen or (C$_1$–C$_4$)-alkyl, or R(1) is phenyl, naphthyl, biphenylyl or (C$_1$–C$_9$)-heteroaryl, the latter linked via C or N, and which are unsubstituted or are substituted by 1 to 3 substituents selected from the group consisting of F, Cl, CF$_3$, CH$_3$, methoxy, hydroxyl, amino, methylamino and dimethylamino, or (R1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$ R(13) and R(14), identically or differently, are —(CH$_2$)$_g$—(CHOH)$_h$—(CH$_2$)$_i$—(CHOH)$_j$—R(17), R(17) is hydrogen, methyl or —(CH$_2$)$_g$—O—(CH$_2$—CH$_2$O)$_h$—R(24), g, h and i, identically or differently, are zero, 1, 2, 3 or 4, j is 1, 2, 3 or 4, R(15) and R(16), identically or differently, are hydrogen, (C$_1$–C$_8$)-alkyl or, together with the carbon atom carrying them, a (C$_3$–C$_8$)-cyclo-alkyl, R(18) is phenyl,
which is unsubstituted or is substituted by 1 to 3 substituents selected from the group consisting of F, Cl, CF$_3$ methyl, methoxy and NR(25)R(26) with R(25) and R(26) being H or (C$_1$–C$_4$)-alkyl, or R(18) is (C$_1$–C$_8$)-heteroaryl,
which is unsubstituted or is substituted as phenyl, or R(18) is (C$_1$–C$_6$)-alkyl,
which is unsubstituted or is substituted by 1 to 3 OH, or R(18) is (C$_3$–C$_8$,)-cycloalkyl, and R(19), R(20), R(21), R(22) and R(23) are hydrogen or methyl, k is zero, 1, 2, 3 or 4, l is zero, 1, 2, 3 or 4, R(24) is H, (C$_1$–C$_6$)-alkyl, (C$_3$–C$_8$,)-cycloalkyl or —C$_m$H$_{2m}$—R(18), m is 1, 2, 3 or 4, R(2) and R(3) are defined as R(1), and R(4) is (C$_1$–C$_3$)-alkyl, F, Cl Br, I, CN or —(CH$_2$)$_n$—(CF$_2$)$_o$—CF$_3$, with the proviso that the compound ortho-chlorobenzoylguanidine hydrochloride is excluded, n is zero or 1, o is zero, 1 or 2, or a pharmaceutically tolerated salt thereof.

2. A compound of the formula I as claimed in claim 1, wherein:

R(1) is H, F, Cl, Br, CN, NO$_2$, (C$_1$–C$_8$)-alkyl, (C$_3$–C$_8$)-cycloalkyl or X$_a$—(CF$_2$)$_c$—CF$_3$, X is oxygen or S, a is zero or 1, c is zero, 1, 2 or 3, or R(1) is —SR(10) or —OR(10), R(10) is —C$_f$H$_{2f}$—(C$_3$–C$_6$)-cycloalkyl,—(C$_1$–C$_9$)-heteroaryl or phenyl, where the —(C$_1$–C$_9$)-heteroaryl or phenyl system is unsubstituted or is substituted by 1 to 3 substituents selected from the group consisting of F, Cl, CF$_3$, CH$_3$, methoxy, hydroxyl, amino, methylamino and dimethylamino, f is zero or 1, or R(1) is phenyl, naphthyl, biphenylyl or (C$_1$–C$_9$)-heteroanyl, the latter linked via C or N, and which are unsubstituted or are substituted by 1 to 3 substituents selected from the group consisting of F, Cl, CF$_3$, CH$_3$, methoxy, hydroxyl, amino, methylamino and dimethylamino, or (R1) is —SR(13), —OR(13), —NHR(13), —NR(13)R(14), —C≡—CR(18), —C[R(19)]=CR(18), R(13) and R(14), identically or differently, are —(CH$_2$)$_g$—(CHOH)$_h$—(CH$_2$)$_i$—(CHOH)$_j$—R(17), R(17) is hydrogen, methyl or —(CH$_2$)$_g$—O—(CH$_2$—CH$_2$O)$_h$—R(24), g, h and i, identically or differently, are zero, 1 or 2, is 1 or 2, R(18) is phenyl, which is unsubstituted or is substituted by 1 to 3 substituents selected from the group consisting of F, Cl, CF$_3$, methyl, methoxy and NR(25)R(26) with R(25) and R(26) being H or (C$_1$–C$_4$)-alkyl, or R(18) is (C$_1$–C$_9$)-heteroaryl, which is unsubstituted or is substituted as phenyl, or R(18) is (C$_1$–C$_6$)-alkyl,
which is unsubstituted or is substituted by 1 to 3 OH, or R(18) is (C$_3$–C$_8$)-cycloalkyl, and R(19) is hydrogen or methyl, R(2) and R(3) are defined as R(1), and R (4) is (C$_1$–C$_2$)-alkyl, F, Cl Br, CN or —(CH$_2$)$_n$—(CF$_2$)$_o$—CF$_3$, with the proviso that the compound ortho-chlorobenzoylguanidine hydrochloride is excluded, n is zero or 1, o is zero or 1, or a pharmaceutically tolerated salt thereof.

3. A compound of the formula I as claimed in claim 1, wherein:

R(1) is H, F, Cl, (C$_1$–C$_8$)-alkyl, (C$_5$–C$_6$)-cycloalkyl or X$_a$—(CF$_2$)$_2$—CF$_3$, X is oxygen, a is zero or 1, c is zero or 1, or R(1) is —SR(10) or —OR(10), R(10) is (C$_4$–C$_6$,)-cycloalkyl, quinolyl, isoquinolyl, pyridyl or phenyl, which is unsubstituted or is substituted by 1 to 3 substituents selected from the group consisting of F, Cl, CF$_3$, CH$_3$, methoxy, hydroxyl, amino, methylamino and dimethylamino, or R(1) is phenyl, quinolyl, isoquinolyl, pyridyl or imidazolyl, bonded via C or N, which are unsubstituted or are substituted by 1 to 3 substituents selected from the group consisting of F, Cl, CF$_3$, CH$_3$, methoxy, hydroxyl, amino, methylamino and dimethylamino, or (R1) is —C≡CR(18), R(18) is phenyl or ($C_5$–$C_6$)-cycloalkyl, R(2) and R(3) are defined as R(1), and R(4) is methyl, F, Cl or $CF_3$, with the proviso that the compound ortho-chlorobenzoylgiuanidine hydrochloride is excluded, or a pharmaceutically tolerated salt thereof.

4. A process for preparing a compound I as claimed in claim 1, which process comprises reacting a compound of the formula II

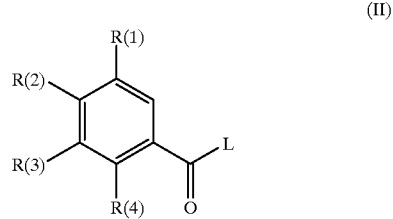

in which R(1) to R(4) have the meanings given in claim 1 and L is a leaving group which is able to be nucleophilically substituted with guanidine.

5. A composition for treating arrhythmias, comprising an effective amount of a compound of formula (I) according to claim 1, together with a pharmaceutically acceptable carrier.

6. A method of treating arrhythmias, comprising administering to a host in need thereof an effective amount of a compound of formula (I) according to claim 1.

7. A composition for treating or preventing cardiac infarction, comprising an effective amount of a compound of formula (I) according to claim 1, together with a pharmaceutically acceptable carrier.

8. A method of treating or preventing cardiac infarction, comprising administering to a host in need thereof an effective amount of a compound of formula (I) according to claim 1.

9. A composition for treating or preventing angina pectoris, comprising an effective amount of a compound of formula (I) according to claim 1, together with a pharmaceutically acceptable carrier.

10. A method of treating or preventing angina pectoris, comprising administering to a host in need thereof an effective amount of a compound of formula (I) according to claim 1.

11. A composition for treating or preventing ischemic conditions of the heart, comprising an effective amount of a compound of formula (I) according to claim 1, together with a pharmaceutically acceptable carrier.

12. A method of treating or preventing ischemic conditions of the heart, comprising administering to a host in need thereof an effective amount of a compound of formula (I) according to claim 1.

* * * * *

UNITED STATES PATENT AND TRADEMARK OFFICE
CERTIFICATE OF CORRECTION

PATENT NO. : 5,965,744
DATED : October 12, 1999
INVENTOR(S) : Weichert et al.

It is certified that error appears in the above-identified patent and that said Letters Patent is hereby corrected as shown below:

On the Title Page, Item [54], in the Title, line 3, "COMPOSITION" should read --COMPOSITIONS--.

On the Title Page, Item [73], in the Assignee, line 1, "Hoeschst" should read --Hoechst--.

In Claim 1, column 11, line 3, "-CR(10O)R(11)R(12)" should read -- -CR(10)R(11)R(12)--.

In Claim 1, column 11, line 9, "dirnethylamino" should read --dimethylamino--.

In Claim 1, column 11, line 32, "$(C_1-C_8)$-alkyl" should read --$(C_1-C_6)$-alkyl--.

In Claim 1, column 11, line 40, "$(C_1-C_8)$-heteroaryl" should read --$(C_1-C_9)$-heteroaryl--.

In Claim 1, column 11, line 45, "$(C_3-C_8,)$-cycloalkyl" should read --$(C_3-C_8)$-cycloalkyl--.

In Claim 1, column 11, line 50, "$(C_1-C_6)$-allcyl" should read --$(C_1-C_6)$-alkyl--.

In Claim 1, column 11, line 50, "$(C_3-C_8,)$-cycloalkyl" should read --$(C_3-C_8)$-cycloalkyl--.

In Claim 2, column 12, line 3, "-$C_fH_{2f}$-$(C_3-C_6)$-cycloalkyl" should read ---$C_fH_{2f}$-$(C_3-C_8)$-cycloalkyl--.

UNITED STATES PATENT AND TRADEMARK OFFICE
CERTIFICATE OF CORRECTION

PATENT NO. : 5,965,744
DATED : October 12, 1999
INVENTOR(S) : Weichert et al.

It is certified that error appears in the above-identified patent and that said Letters Patent is hereby corrected as shown below:

In Claim 2, column 12, line 12, "heteroanyl" should read --heteroaryl--.
In Claim 3, column 12, line 57, "($C_4$-$C_6$,)-cycloalkyl" should read --($C_4$-$C_6$)-cycloalkyl--.

In Claim 3, column 13, line 7, "chlorobenzoylgiuanidine" should read --chlorobenzoylguanidine--.

Signed and Sealed this

Twelfth Day of December, 2000

Q. TODD DICKINSON

*Attest:*

*Attesting Officer*   *Director of Patents and Trademarks*